(12) United States Patent
Aase et al.

(10) Patent No.: US 7,678,050 B2
(45) Date of Patent: Mar. 16, 2010

(54) METHOD AND APPARATUS FOR DETECTING CARDIAC EVENTS

(75) Inventors: Svein Arne Aase, Trondheim (NO);
Sigmund Frigstad, Trondheim (NO);
Hans Garmann Torp, Trondheim (NO)

(73) Assignee: General Electric Company, Schenectady, NY (US)

( * ) Notice: Subject to any disclaimer, the term of this patent is extended or adjusted under 35 U.S.C. 154(b) by 944 days.

(21) Appl. No.: 11/064,645

(22) Filed: Feb. 24, 2005

(65) Prior Publication Data

US 2006/0058673 A1 Mar. 16, 2006

Related U.S. Application Data

(60) Provisional application No. 60/604,161, filed on Aug. 24, 2004.

(51) Int. Cl.
*A61B 8/00* (2006.01)
(52) U.S. Cl. .................. 600/437; 600/438; 600/450; 600/453
(58) Field of Classification Search .............. 600/437, 600/513, 528, 450, 508, 481, 453, 454, 438
See application file for complete search history.

(56) References Cited

U.S. PATENT DOCUMENTS

| 5,139,020 | A | * | 8/1992 | Koestner et al. ............... 607/24 |
| 5,454,838 | A | * | 10/1995 | Vallana et al. ................. 607/19 |
| 5,622,174 | A | * | 4/1997 | Yamazaki ................... 600/441 |
| 6,592,522 | B2 | | 7/2003 | Bjaerum et al. |
| 2003/0013962 | A1 | * | 1/2003 | Bjaerum et al. ............. 600/443 |
| 2004/0254486 | A1 | | 12/2004 | Heimdal |

OTHER PUBLICATIONS

Kalmanson, D. et al., "Normal pattern and physiological significance of mitral valve flow velocity recorded using transseptal directional Doppler ultrasound catheterization", British Heart Journal, 1975, vol. 37, pp. 249-256.*

W.N. McDicken et al., "Colour Velocity Imaging of the Myocardium", Ultrasound in Medicine and Biology, 1992, pp. 651-654, vol. 18, Nos. 6/7, Pergamon Press Ltd., U.S.A.

J. Kirkhorn et al., "A New Technique for Improved Spatial Resolution in High Frame Rate Color Doppler Imaging", IEEE Ultrasonics Symposium, 2003, pp. 1947-1950, IEEE, U.S.A.

L.N. Bohs, "A Novel Method for Angle Independent Ultrasonic Imaging of Blood Flow and Tissue Motion", IEEE Transactions on Biomedical Engineering, Mar. 1991, pp. 280-286, vol. 38, No. 3, IEEE, U.S.A.

(Continued)

*Primary Examiner*—Eric F Winakur
*Assistant Examiner*—Katherine L Fernandez
(74) *Attorney, Agent, or Firm*—Dean D. Small; Small Patent Law Group

(57) ABSTRACT

A method and apparatus for detecting cardiac events. Ultrasonic data comprising a heart cycle is acquired by a probe. Tissue velocities associated with the ultrasonic data are detected. One of a maximum and a minimum value is detected based on the tissue velocities. A time within the heart cycle associated with the maximum or minimum value is determined, and a cardiac event is detected with respect to the time within the heart cycle and the maximum or minimum value.

24 Claims, 11 Drawing Sheets

OTHER PUBLICATIONS

F. Weidemann et al., Defining the Transmurality of a Chronic Myocardial Infarction by Ultrasonic Strain-Rate Imaging, Implications for Identifying Intramural Viability, An "Experimental Study", Circulation, Feb. 18, 2003, pp. 883-888, American Heart Association, Inc., U.S.A.

C. Pislaru et al., "Higher Myocardial Strain Rates During Isovolumic Relaxation Phase Than During Ejection Characterize Acutely Ischemic Myocardium", Journal of the American College of Cardiology, 2002, pp. 1487-1494, vol. 40, No. 8, Elsevier Science, U.S.A.

T. Kukulski et al., "Identification of Acutely Ischemic Myocardium Using Ultrasonic Strain Measurements", Journal of the American College of Cardiology, 2003, pp. 810-819, vol. 41, No. 5, Elsevier Science Inc., U.S.A.

H. Kanai et al., "Myocardial Rapid Velocity Distribution", Ultrasound in Medicine & Biology, 2001, pp. 481-498, vol. 27, No. 4, Elsevier Science Inc., U.S.A.

A. Heimdal et al., "Real-Time Strain Rate Imaging of the Left Ventricle by Ultrasound", Journal of the American Society of Echocardiography, 1998, pp. 1013-1019, vol. 11, No. 11, American Society of Echocardiography, U.S.A.

J. Gorcsan III et al., "Usefulness of Echocardiographic Tissue Synchronization Imaging to Predict Acute Response to Cardiac Resynchronization Therapy", The American Journal of Cardiology, May 1, 2004, pp. 1178-1181, vol. 93, Elsevier Science, U.S.A.

C. Pislaru et al., "Ultrasound Imaging of Altered Myocardial Stiffness, Stunned Versus Infarcted Reperfused Myocardium", Circulation, Jun. 15, 2004, pp. 2905-2910, American Heart Association, U.S.A.

A. Stoylen, S. Malm, S. Aase and E. Sagberg, "Aortic valve closure can be timed by tissue doppler", *Abstract accepted for Euroecho 8, Athens*, Dec. 1-4th 2004, Eur J Echocardiography (2004), pp. S1, S159.

J. D'hooge, A. Heimdal, F. Jamal, T. Kukulski, B. Bijnens, F. Rademakers, L. Hatle, and G. Sutherland, "Regional strain and strain rate measurements by cardiac ultrasound: Principles, implementation and limitations," *European Journal of Echocardiography* (2000) 1, pp. 154-170.

A.H. Torp, S.I. Rabben, A. Stoylen, H. Ihlen, K. Andersen, L. Brodin and B. Olstad, "Automatic detection and tracking of left ventricular landmarks in echocardiography," *Proceedings IEEE International Ultrasonics, Ferroelectrics, and Frequency Control 50th Anniversary Joint Conference*, 2004, pp. 474-477.

* cited by examiner

METHOD AND APPARATUS FOR DETECTING CARDIAC EVENTS

CROSS REFERENCE TO RELATED APPLICATIONS

The application relates to and claims priority from provisional patent application Ser. No. 60/604,161, titled "Method and Apparatus for Detecting Atrial Valve Closure", filed Aug. 24, 2004, the complete subject matter of which is expressly hereby incorporated herein in its entirety.

BACKGROUND OF THE INVENTION

This invention relates generally to detecting cardiac events, and more particularly, to detecting the closure of the aortic valve.

To evaluate events in specific parts of the cardiac cycle, information about the transitions between the phases is important. Aortic valve closure (AVC) is an important event in the time cycle of the left ventricle, marking the transition from end of ejection to start of diastole. Several methods for determining the timing of AVC exist. Echocardiographic methods include parasternal M-mode of the aortic valve and pulsed/continuous Doppler of the blood flow through the aortic valve. Other methods include phonocardiography of the second heart sound and empirical regression formulas based on heart rate.

Echocardiographic recordings from the apical position provide most tissue Doppler information used in analysis, while the echocardiographic methods for determining the timing of AVC usually use other views or recording modalities, hence giving timing information in separate heart cycles. The heart rate varies from cycle to cycle, and with this heart rate variability the relation between systole and diastole changes, thus changing the timing of the AVC relative to the heart cycle.

Therefore, a need exists for method and apparatus for determining AVC directly, using apical views from the same heart cycle as used in analysis. Certain embodiments of the present invention are intended to meet these needs and other objectives that will become apparent from the description and drawings set forth below.

BRIEF DESCRIPTION OF THE INVENTION

A method for detecting cardiac events comprises acquiring ultrasonic data comprising a heart cycle. Tissue velocities are detected associated with the ultrasonic data. A value based on the tissue velocities is detected. The value is one of a maximum value and a minimum value. A time associated with the value is identified within the heart cycle. A cardiac event is detected with respect to the value and the time.

An apparatus for detecting cardiac events comprises an ultrasonic probe for transmitting and receiving ultrasonic data. An ECG device acquires ECG data associated with the ultrasonic data. A signal processor processes the ultrasonic data and detects one of a maximum and minimum value based on tissue velocities associated with the ultrasonic data. The signal processor identifies a time associated with one of the maximum and minimum value and detects a cardiac event with respect to the time and the value.

A method for detecting cardiac events comprises acquiring ultrasonic data comprising a heart cycle. A first maximum or minimum value is detected based on tissue velocities associated with the ultrasonic data. A search interval comprising a portion of the heart cycle is located based on the first maximum or minimum value. A second maximum or minimum value is detected based on the tissue velocities within the search interval. The second maximum or minimum value is used to detect a cardiac event.

The foregoing summary, as well as the following detailed description of certain embodiments of the present invention, will be better understood when read in conjunction with the appended drawings. It should be understood that the present invention is not limited to the arrangements and instrumentality shown in the attached drawings.

DETAILED DESCRIPTION OF THE INVENTION

Figure 1:
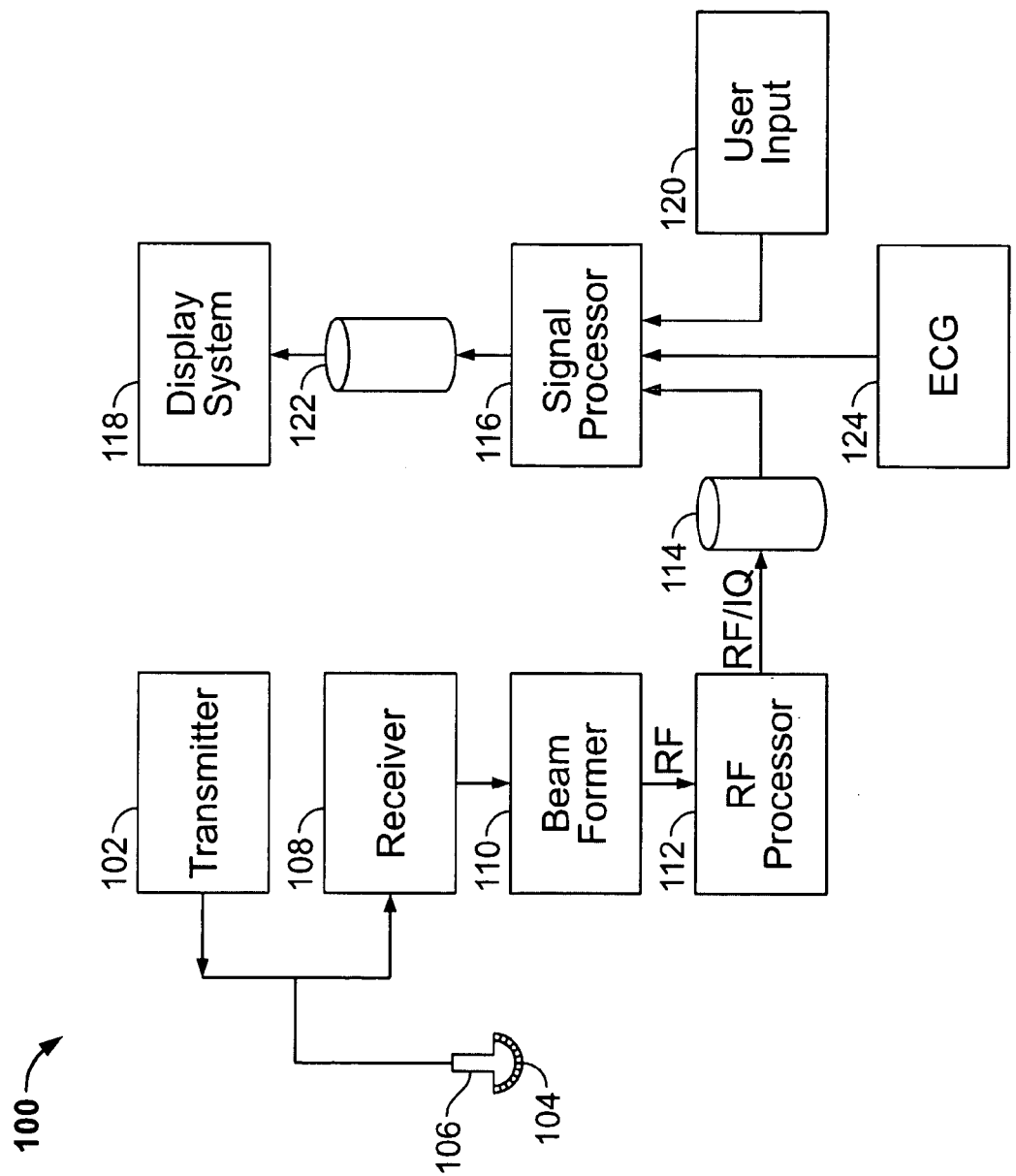
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives transducers 104 within a probe 106 to emit pulsed ultrasonic signals into a body. A variety of geometries may be used. The ultrasonic signals are back-scattered from structures in the body, like blood cells or muscular tissue, to produce echoes which return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage. A user input 120 may be used to input patient data, scan parameters, a change of scan mode, and the like.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information is displayed on the display system 118 at a slower frame-rate. An image buffer 122 is included for storing processed frames of acquired ultrasound information that are not scheduled to be displayed immediately. The image frames may be stored as data sets. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium. Additional data may be acquired such as ECG data from a patient via multiple leads through an ECG device 124. ECG data is often acquired simultaneously with ultrasonic data.

Figure 2:
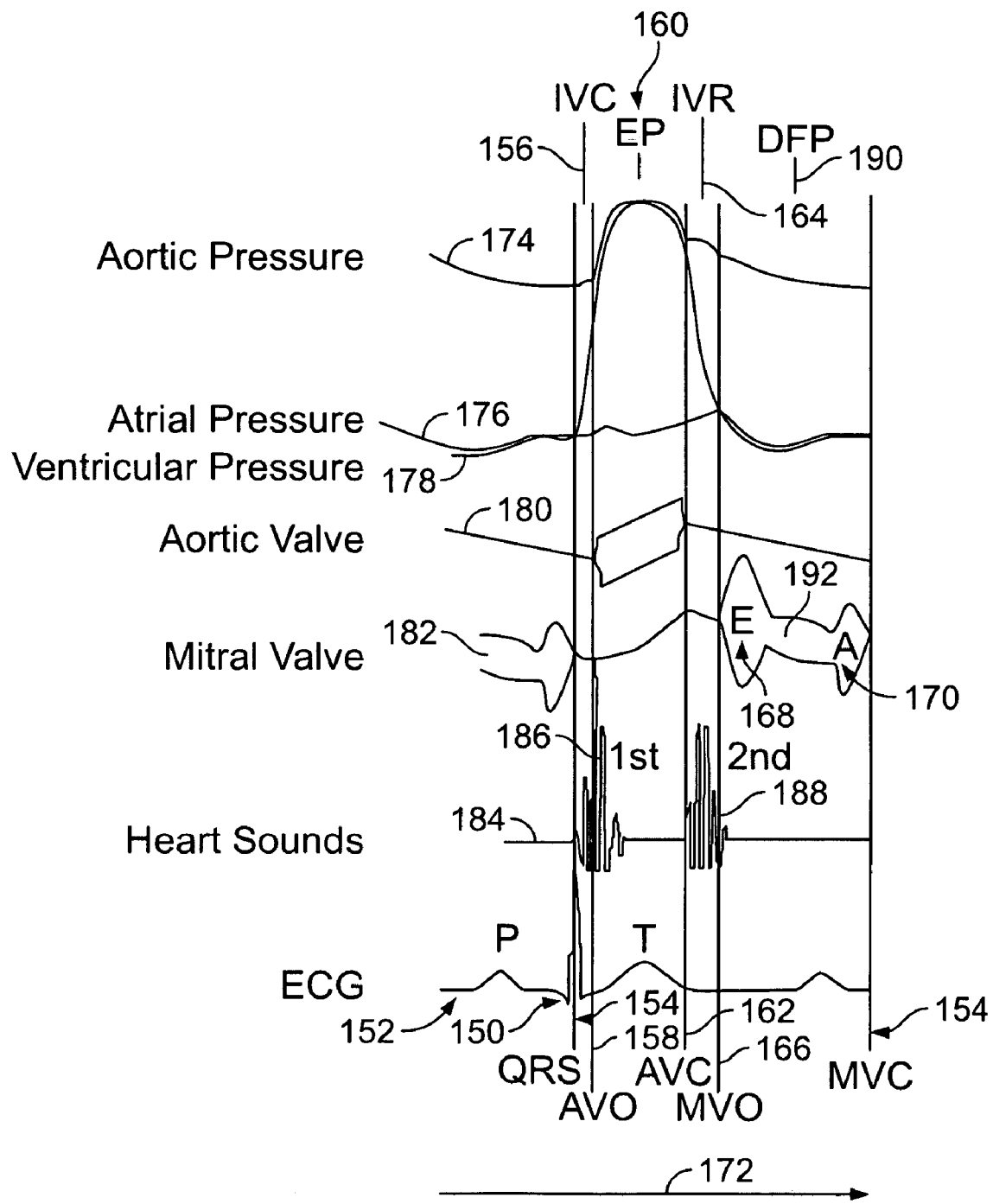
FIG. 2 illustrates multiple waveforms representing different activities over time during a heart cycle in accordance with an embodiment of the present invention.

FIG. 2 illustrates multiple waveforms representing different activities over time 172 during a heart cycle in accordance with an embodiment of the present invention. An aortic pressure waveform 174, an atrial pressure waveform 176, and a ventricular pressure waveform 178 are illustrated. The aortic, atrial and ventricular pressure waveforms 174, 176 and 178 represent a measure of the blood pressure. An aortic valve waveform 180 and mitral valve waveform 182 indicate the opening and closing of the respective valves over time 172. Heart sounds 184, as recorded by phonocardiography, are illustrated for reference only as first sound 186 and second sound 188. An ECG trace 152, as recorded by ECG device 124, is also illustrated.

The heart cycle is divided into different phases defined by the opening and closure of the mitral and aortic valves, which may also be referred to as cardiac events. Left ventricular contraction starts roughly at the start of QRS complex 150 on the ECG 152, which represents the electrical activation of the ventricles. Mitral valve closure (MVC) 154 marks the end of diastolic filling period (DFP) 190, and the start of isovolumic contraction (IVC) 156. MVC 154 is illustrated at two different locations on FIG. 2. Aortic valve opening (AVO) 158 marks the end of IVC 156 and the start of the ejection period (EP) 160. Aortic valve closure (AVC) 162 marks the end of EP 160 and the start of isovolumic relaxation (IVR) 164. IVR 164 ends with mitral valve opening (MVO) 166, marking the start of the DFP 190. The DFP 190 has three phases, early filling (E wave) 168 due to continuing ventricular relaxation, a purely passive flow phase called diastasis 192, and late filling due to atrial contraction (A wave) 170.

The QRS complex 150 starts close to the same time as MVC 154, and may start shortly before or shortly after MVC 154. The detection of the first part of the QRS complex 150 is dependent on the position of the electrode on the chest. The leading edge of the R-peak can be used as a rough reference point for the start of the contraction cycle.

Ultrasound tissue Doppler imaging (TDI) uses the Doppler effect to measure tissue velocities. The velocities are presented in a two-dimensional color image similar to Doppler color flow imaging (CFI); however, a higher frame rate is possible with TDI compared with CFI. For example, TDI frame rates of 160 frames/second acquired and displayed simultaneously with gray scale images at 40 frames/second for apical images covering the entire left ventricle are achievable. Thus, the AVC 162 may be manually detected in the entire base of the left ventricle using apical views (four-chamber, two-chamber and long-axis views), as described in patent application Ser. No. 10/796,834, titled "Trigger Extraction from Ultrasound Doppler Signals", filed Mar. 9, 2004, the complete subject matter of which is expressly hereby incorporated herein in its entirety.

Figure 3:
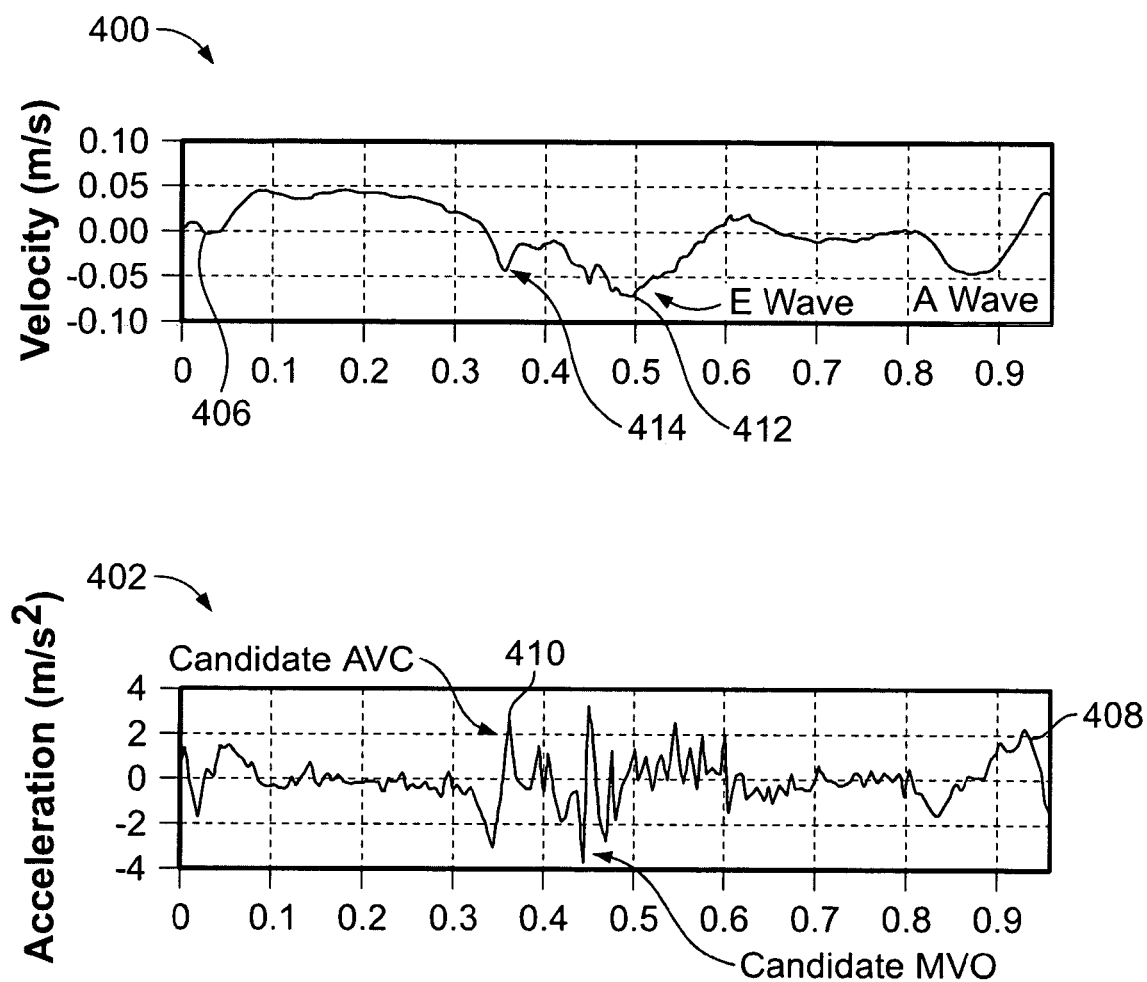
FIG. 3 illustrates TDI velocity and acceleration graphs of the left ventricle based on apical images in accordance with an embodiment of the present invention.

FIG. 3 illustrates TDI velocity and acceleration graphs 400 and 402 of the left ventricle based on apical images in accordance with an embodiment of the present invention. Referring to velocity curve 406 of the velocity graph 400 and FIG. 2, the normal tissue velocities of the left ventricle as measured by TDI are roughly positive during IVC 156 and EP 160, negative during E wave 168 and A wave 170, while being close to zero during diastasis 190.

With TDI it is possible to capture and extract the quantitative velocities used in a tissue Doppler image at each point in the image at each time step. The TDI velocity of a tissue sample represents the velocity of the tissue in the direction of the ultrasound beam. Abrupt changes in the directions of tissue motion, such as AVC 162, are visible using TDI. As the open aortic valve suddenly closes, the aortic valve causes a brief motion towards the apically positioned probe 106. Velocities towards the probe 106 are defined positive, and thus the aortic valve closure results in positive acceleration. In velocity/time curves from basal segments this can be seen by the onset of the IVR 164 typically having positive acceleration as illustrated in FIG. 3 as the velocity curve 406 rises at approximately point 414. Referring also to the acceleration curve 408 of the acceleration graph 402, the mitral valve opens between the point of AVC 410 and E wave minimum value 412.

Figure 4:
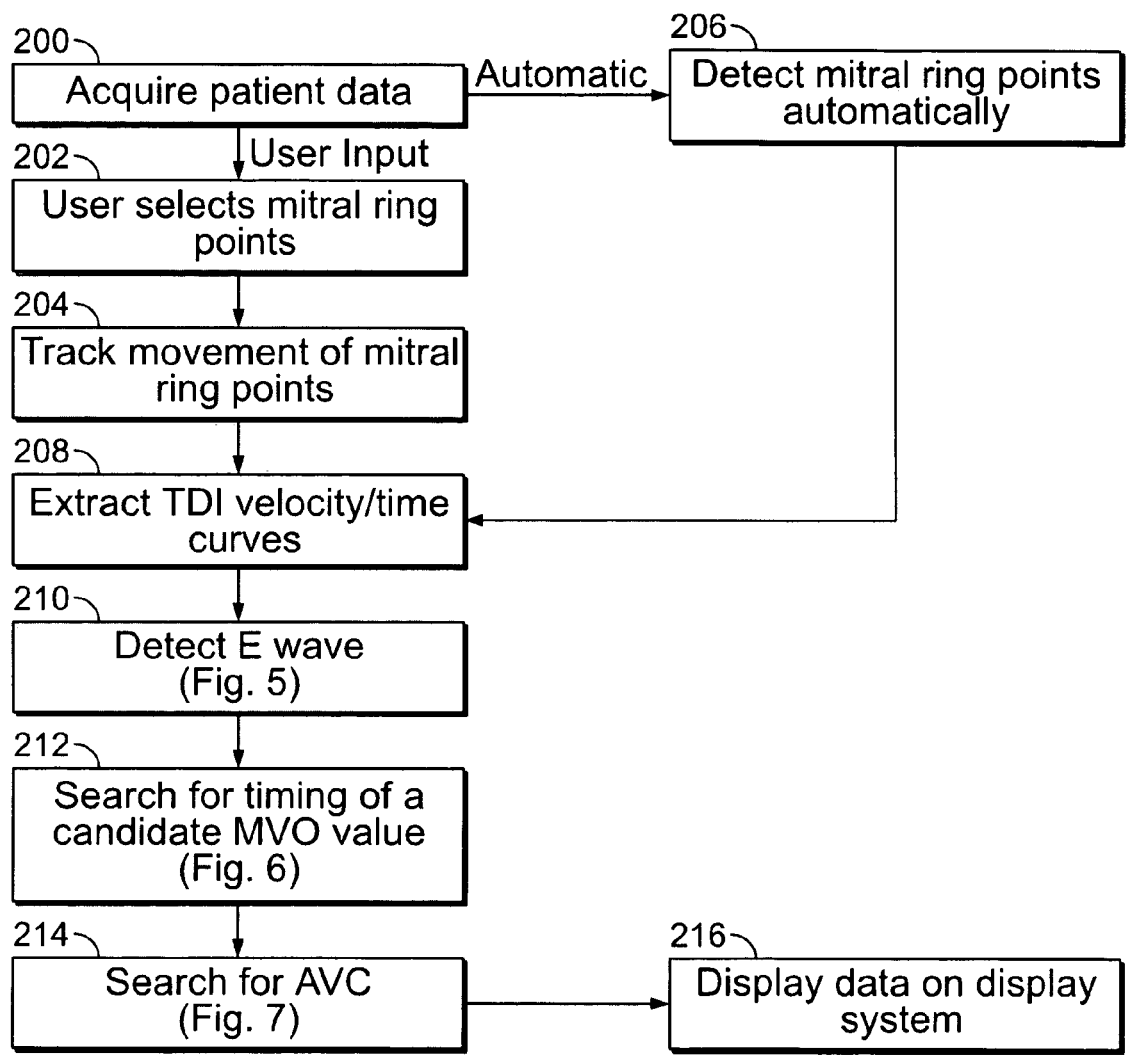
FIG. 4 illustrates a method for detecting AVC using TDI data from apical views in accordance with an embodiment of the present invention.
Figure 5:
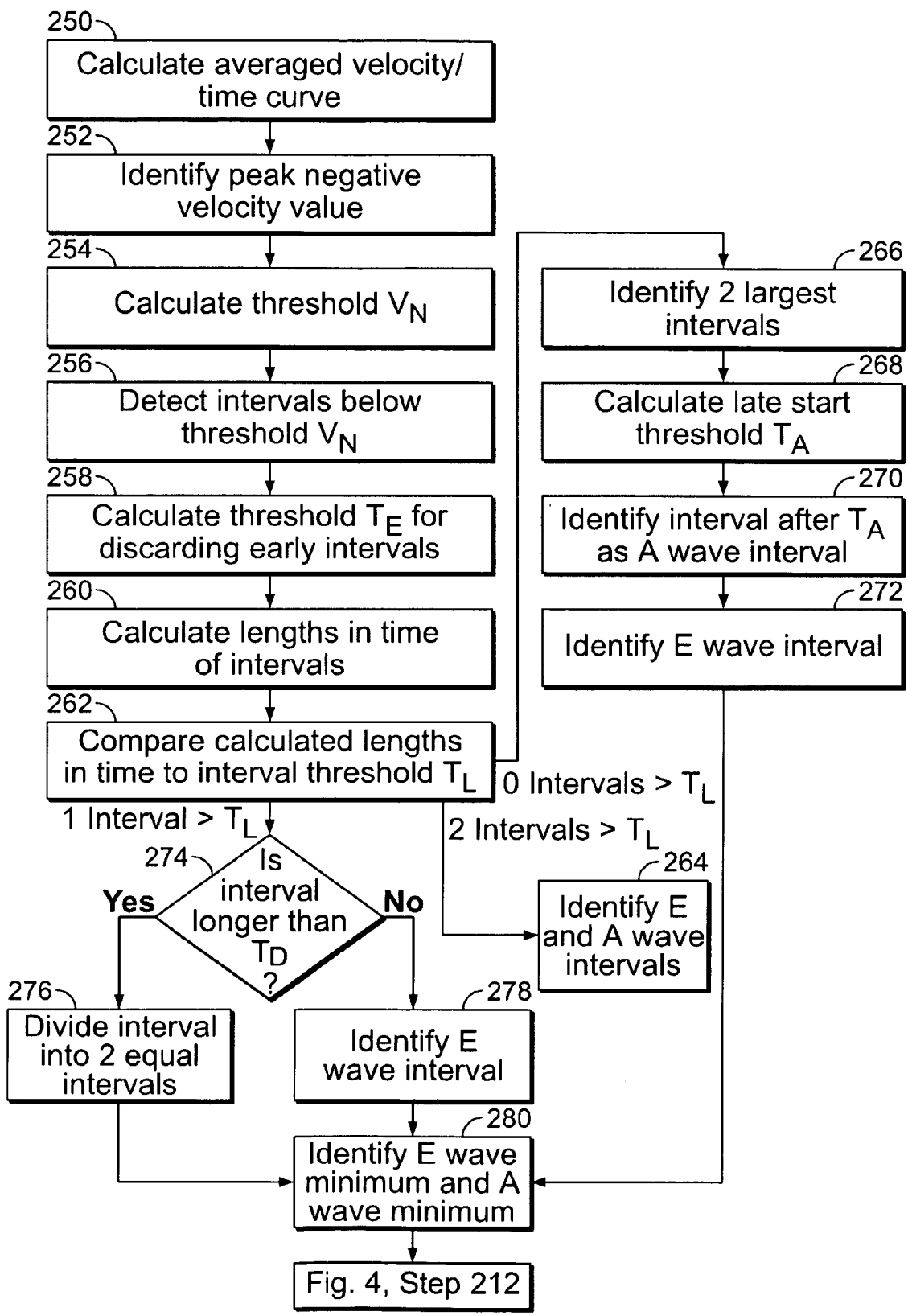
FIG. 5 illustrates a method for detecting the E wave in accordance with an embodiment of the present invention.
Figure 6:
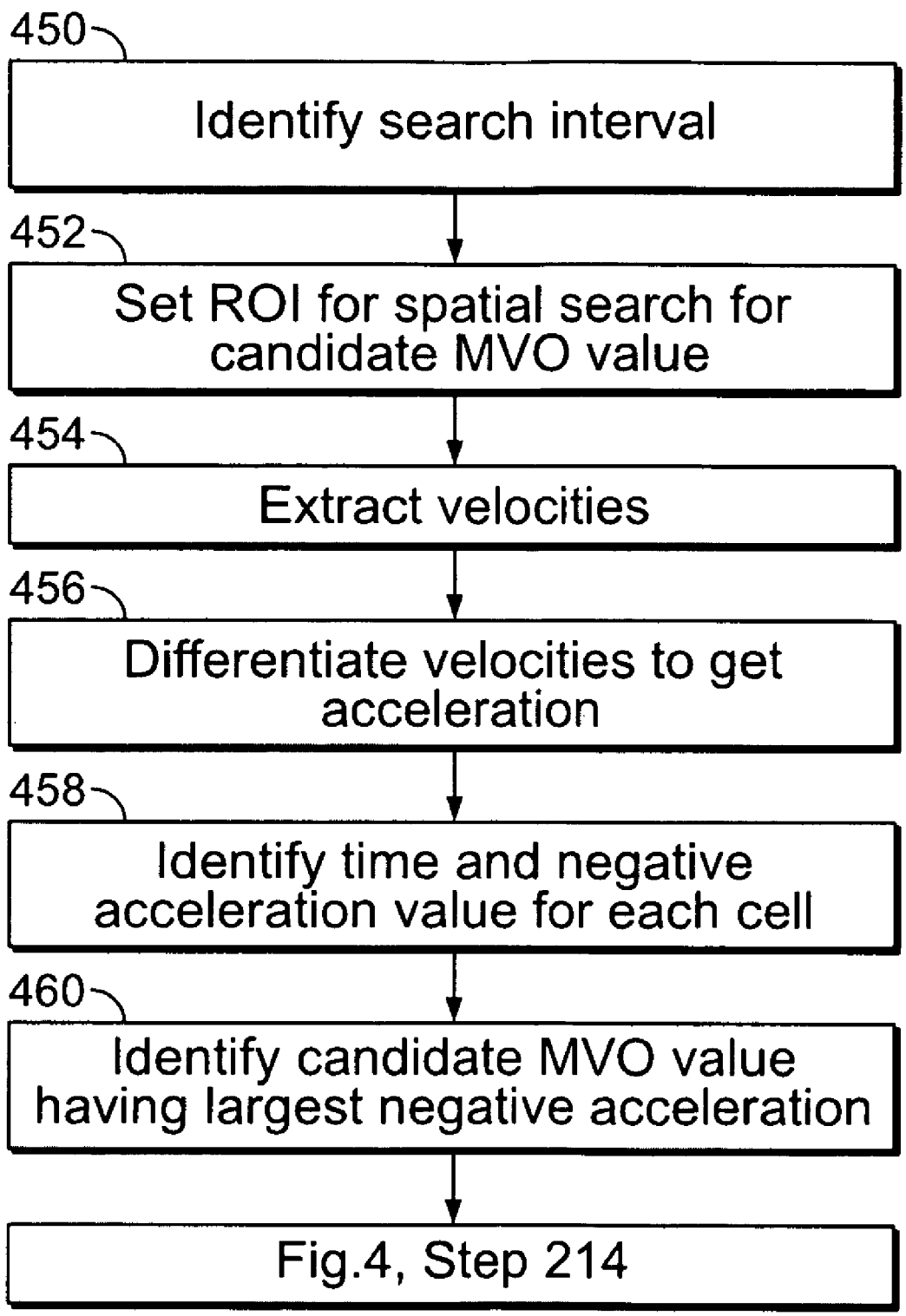
FIG. 6 illustrates a method for detecting a candidate MVO value using spatial and temporal searching in accordance with an embodiment of the present invention.
Figure 7:
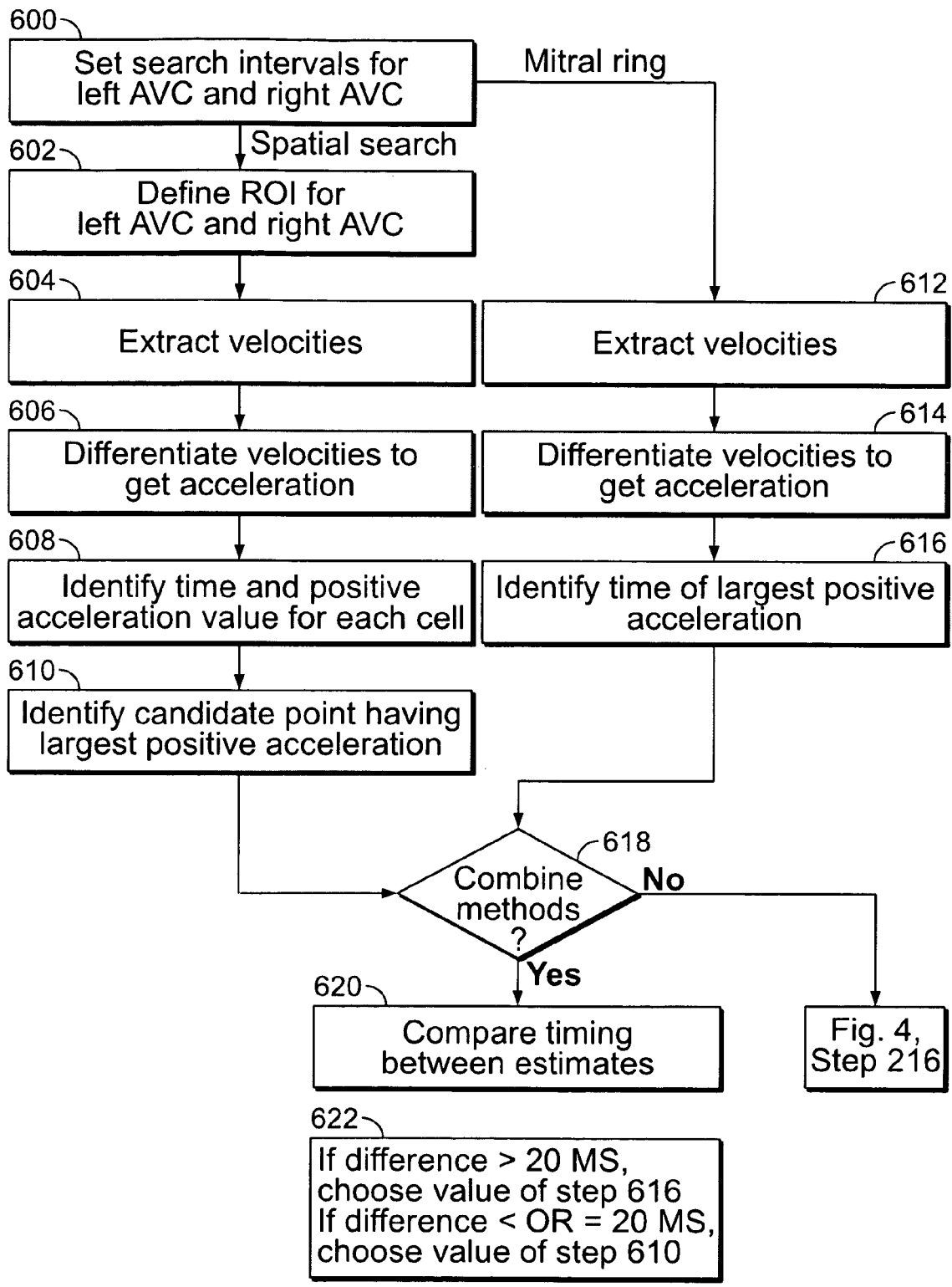
FIG. 7 illustrates a method for searching for AVC in accordance with an embodiment of the present invention.

FIG. 4 illustrates a method for detecting AVC 162 using TDI data from apical views in accordance with an embodiment of the present invention. FIGS. 5, 6 and 7 illustrate detailed steps within the method of FIG. 4. FIG. 5 illustrates a method for detecting the E wave 168 in accordance with an embodiment of the present invention. FIG. 6 illustrates a method for detecting a candidate MVO value using spatial and temporal searching in accordance with an embodiment of the present invention. FIG. 7 illustrates a method for searching for AVC 162 in accordance with an embodiment of the present invention.

Some steps within the method may be fully automated while other steps may require input from the user via user input 120. The mitral valve has leaflets which attach to a mitral ring between the left atrium and the left ventricle. The method utilizes the motion of points identified on the mitral ring which can be located in all apical views. Mitral ring points produce strong echoes and move significantly during the cardiac cycle. Therefore, velocity/time curves from tracked mitral ring points are robust with respect to noise and contain large velocity values compared to other parts of the heart within the ultrasound image.

In step 200, the ultrasound system 100 acquires patient cardiac data over one or more heart cycles using the probe 106. Patient cardiac data may comprise apical views of ultrasonic data acquired using TDI. Simultaneously, the ultrasound system 100 may acquire ECG data of the patient's heart cycles through the ECG device 124. The patient cardiac data is saved to the buffer 114 for processing by the signal processor 116. The patient cardiac data may be processed immediately or after a patient has left the examination.

Figure 8:
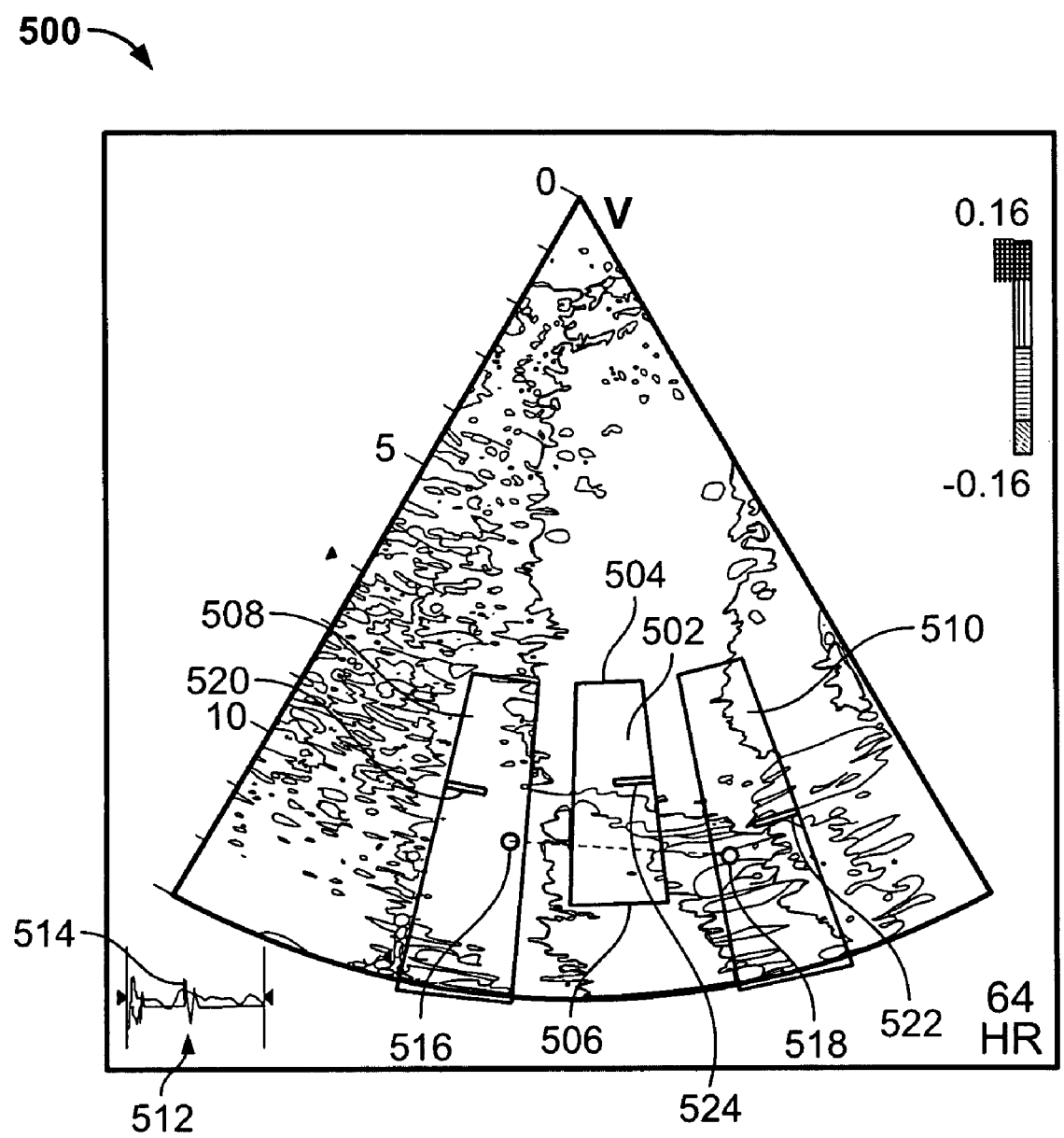
FIG. 8 illustrates a frame of apical TDI ultrasonic data acquired during a heart cycle in accordance with an embodiment of the present invention.

FIG. 8 illustrates a frame 500 of apical TDI ultrasonic data acquired during a heart cycle in accordance with an embodiment of the present invention. The frame 500 is displayed on the display system 118 and the user input 120 may be used to scroll through all or a portion of the acquired frames of data prior to selecting the desired frame. An ECG trace 512 may be illustrated on the frame 500. A marker 514 on the ECG trace 512 indicates where frame 500 is located within the heart cycle.

Returning to FIG. 4, flow passes to step 202 if the user is going to input data. In step 202, the user selects two mitral ring points 516 and 518 on the frame 500 of TDI ultrasonic data using the user input 120.

In step 204, the signal processor 116 tracks the movement of the mitral ring points 516 and 518 through one cardiac cycle. By way of example only, the signal processor 116 may utilize a speckle tracking algorithm (of B-mode images), tissue Doppler, or other method to track the mitral ring points 516 and 518. It should be understood that cardiac landmarks other than the mitral ring points 516 and 518 may be identified and tracked throughout the heart cycle.

Returning to step 200, if the two mitral ring points 516 and 518 are to be automatically detected, flow passes to step 206. In step 206, the signal processor 116 detects the two mitral ring points 516 and 518 and tracks the movement of the two mitral ring points 516 and 518 through one cardiac cycle using a mitral ring detector algorithm. (Torp, et al.)

The method flows from steps 204 and 206 to step 208. In step 208, the signal processor 116 extracts TDI velocity/time curves originating from the mitral ring points 516 and 518.

Figure 9:
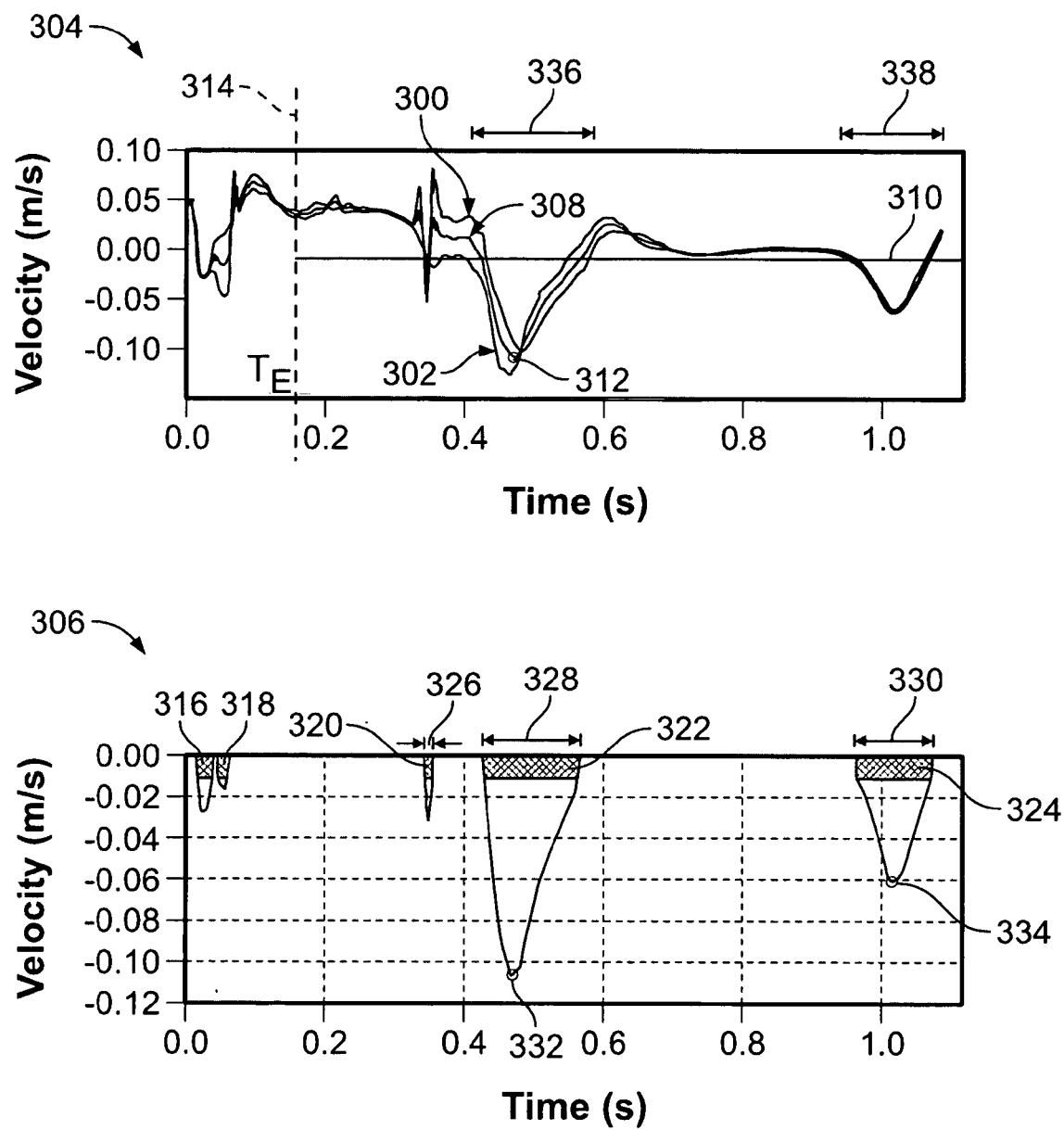
FIG. 9 illustrates velocity/time graph and associated interval graph in accordance with an embodiment of the present invention.

FIG. 9 illustrates velocity/time graph 304 and associated interval graph 306 in accordance with an embodiment of the present invention. The TDI velocity/time curves extracted in step 208 are illustrated as first velocity/time curve 300 and second velocity/time curve 302.

In step 210, the signal processor 116 detects the E wave 168 (FIG. 2). The method to detect the E wave 168 is illustrated in FIG. 5. By detecting the E wave 168, a more robust AVC 162 detection may be accomplished. It should be understood that other methods may be used to detect the E wave 168.

Turning to FIG. 9, the E wave 168 is represented in the first and second velocity/time curves 300 and 302 of the mitral ring points 516 and 518 as a rather large negative dip over a time period 336. Following the E wave dip, a second negative dip over a time period 338 representing the A wave 170 can be seen if the A wave 170 is present within the heart cycle. The time periods 336 and 338 are provided as reference only, and are not used to indicate the precise positioning of the E wave 168 and A wave 170.

Turning to FIG. 5, in step 250, the signal processor 116 calculates averaged velocity/time curve 308 (FIG. 9) by averaging the first velocity/time curve 300 and the second velocity/time curve 302. By averaging the first and second velocity/time curves 300 and 302, a potential case where the E wave 168 is visible in only one of the first and second velocity/time curves 300 and 302 is avoided.

In step 252, the signal processor 116 identifies a peak negative velocity value 312 on the averaged velocity/time curve 308. In step 254, the signal processor 116 calculates a threshold value $V_N$. The threshold value $V_N$ is illustrated as threshold 310, a horizontal line on the velocity/time graph 304. For example, the threshold value $V_N$ may be 10 percent of the peak negative velocity value 312. It should be understood that other values of the threshold value $V_N$ may be used. Therefore, if the averaged velocity/time curve 308 does not rise above zero between the E wave 168 and the A wave 170, a potential case in which two intervals are detected as a single interval may be avoided.

In step 256, the signal processor 116 detects intervals of the averaged velocity/time curve 308 which are below the threshold 310. The interval graph 306 illustrates intervals 316, 318, 320, 322 and 324.

In step 258, the signal processor 116 calculates a threshold $T_E$ 314 for discarding early intervals. For example, the threshold $T_E$ 314 may be calculated as 14 percent of the total heart cycle length and is illustrated as a vertical line on FIG. 9. Detected intervals near QRS 150 of the ECG trace 152 correspond to events in the IVC 156, or early systolic phase, and are not needed for the identification of the E wave 168. Therefore, intervals 316 and 318, which occur prior to the threshold $T_E$ 314, are discarded.

In step 260, the signal processor 116 calculates lengths in time of the intervals 320, 322 and 324. The lengths in time 326, 328 and 330 correspond to intervals 320, 322 and 324, respectively.

In step 262, the signal processor 116 compares the lengths in time 326, 328 and 330 to a threshold for interval length, interval threshold $T_L$. By way of example only, the interval threshold $T_L$ may be 0.065 seconds. Therefore, length in time 326 is less than the interval threshold $T_L$ and is discarded. Lengths in time 328 and 330 are both greater than the interval threshold $T_L$.

If two of the lengths in time 328 and 330 are greater than the interval threshold $T_L$, flow passes to step 264. In step 264, the signal processor 116 identifies the interval which occurs first in time as the E wave interval. Thus, in FIG. 9, the interval 322 is identified as the E wave interval and the interval 324 is identified as the A wave interval.

Returning to step 262, if none of the lengths in time 326, 328 and 330 are greater than the interval threshold $T_L$, flow passes to step 266. In step 266, the signal processor 116 identifies the two largest intervals of the lengths in time 326, 328 and 330. In FIG. 9, the two largest intervals are intervals 322 and 324.

In step 268, the signal processor 116 calculates a late start threshold $T_A$ for identifying the A wave 170 when the A wave 170 starts late in the heart cycle. By way of example only, the late start threshold $T_A$ may be calculated as 80 percent of the total heart cycle length.

In step 270, the signal processor 116 identifies the interval 322 or 324 which occurs after the late start threshold $T_A$ as the A wave interval. Therefore, in step 272, the first interval to occur within the heart cycle is identified as the E wave interval. Thus, interval 322 is identified as the E wave interval and interval 324 is identified as the A wave interval.

Returning to step 262, if only one interval 322 and 324 exceeds the interval threshold $T_L$, flow passes to step 274.

Figure 10:
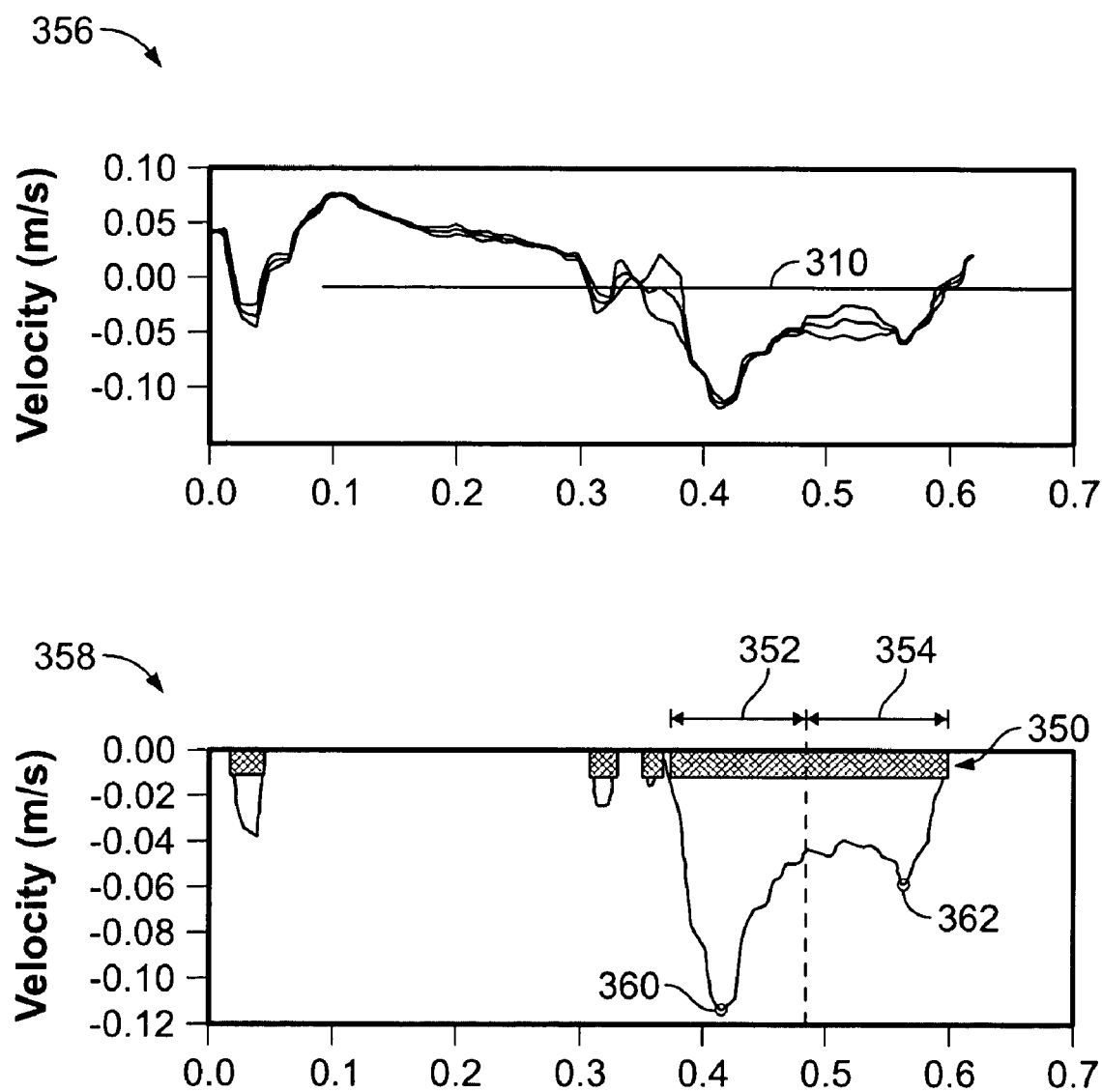
FIG. 10 illustrates velocity/time graph and associated interval graph in accordance with an embodiment of the present invention.

FIG. 10 illustrates velocity/time graph 356 and associated interval graph 358 in accordance with an embodiment of the present invention. The interval graph has a single interval 350 which exceeds the interval threshold $T_L$. Returning to FIG. 5, in step 274 the signal processor 116 compares the interval 350 to a dividing threshold $T_D$. For example, the dividing threshold $T_D$ may be 0.140 seconds. The interval 350 is longer than the dividing threshold $T_D$, and flow passes to step 276.

In step 276, the signal processor 116 divides the interval 350 into two equal parts along the time axis of the heart cycle. The first search interval 352 is the E wave interval and the second search interval 354 is the A wave interval.

Returning to step 274, if the interval 350 which exceeds the interval threshold $T_L$ is less than the dividing threshold $T_D$, flow passes to step 278. In step 278, the signal processor 116 identifies the interval 350 as the E wave interval. There is no A wave 170 present (not shown). For example, in patients with higher heart rates, a single interval which is shorter than the dividing threshold $T_D$ indicates that the E and A waves 168 and 170 have been joined into one wave.

Once the E wave interval and A wave interval (if present) are detected in steps 264, 272, 276, and 278, flow passes from each of these steps to step 280. In step 280, the signal processor 116 identifies a negative peak value within the E wave interval and the A wave interval (if present). For example, if the interval associated with the E wave 168 was identified as interval 322 (FIG. 9) having length in time 328, the signal processor 116 searches the averaged velocity/time curve 308 over the length in time 328 for the negative peak value. The negative peak value is identified in FIG. 9 as E wave minimum value 332. If the interval associated with the A wave 170 was identified as interval 324 having length in time 330, the signal processor 116 searches the averaged velocity/time curve 308 over the length in time 330 for the negative peak value. The negative peak value is identified as A wave minimum value 334. Similarly, in FIG. 10, the negative peak value is identified in the first search interval 352 as E wave minimum value 360, and the negative peak value is identified in the second search interval 354 as A wave minimum value 362.

The method then returns to step 212 of FIG. 4. In step 212, the signal processor 116 searches for the timing of a candidate MVO value.

Figure 11:
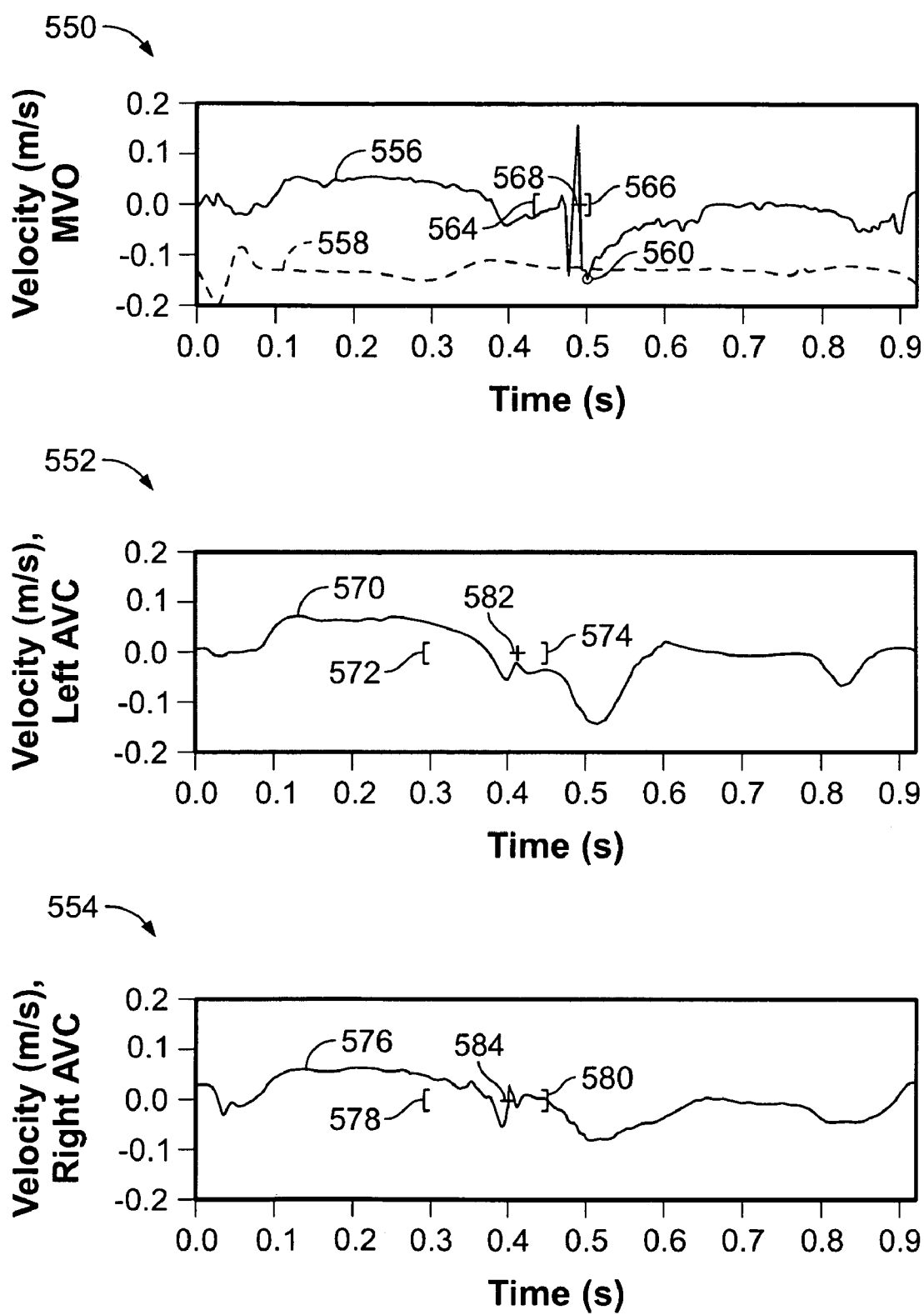
FIG. 11 illustrates TDI velocity graphs based on apical views in accordance with an embodiment of the present invention.

FIG. 11 illustrates TDI velocity graphs 550, 552 and 554 based on apical views in accordance with an embodiment of the present invention. A TDI velocity curve 556 of values within a region of interest comprising at least a part of the mitral valve and scaled ECG 558 are illustrated on the TDI velocity graph 550. The location of an E wave minimum value 560 has been identified as previously discussed. The TDI velocity graphs 552 and 554 illustrate velocity/time curves 570 and 576 based on left and right AVC regions of interest. The regions of interest are defined on FIG. 8 and will be further discussed below.

Turning to FIG. 6, in step 450, the signal processor 116 sets a temporal search interval in which to search for a candidate MVO value. The temporal search interval is illustrated by brackets 564 and 566. The bracket 564 indicates the start of the temporal search interval, just at or prior to the start of the E wave interval, and the bracket 566 indicates the end of the temporal search interval at the timing of the E wave minimum value 560. The temporal search interval covers a period of time during the heart cycle and is translated into corresponding frames of the acquired ultrasound data, such as the frame 500 of FIG. 8.

In step 452, the signal processor 116 sets a region of interest (ROI) 502 defining a region within the frame 500 for spatial searching for a candidate MVO value. Therefore, the ROI 502 defines a subset of ultrasonic data within the frame 500. The MVO 166 is not visible in all areas of the frame 500. Therefore, it is not necessary to search the entire frame 500 for the candidate MVO value 568. The ROI 502 should cover the portion of the mitral valve that is opening at the time when the mitral valve is opening. Therefore, the ROI 502 is defined midway spatially between the tracked mitral ring points 516 and 518. The upper edge 504 of the ROI 502 is limited to be in the lower ⅗ part of the frame 500 and the lower edge 506 of the ROI 502 is located at the deepest position of the tracked mitral ring points 516 and 518 within the heart cycle. The width of the ROI 502 may be based on the width of the ultrasound beam.

In step 454, the signal processor 116 extracts the velocities for all cells within the ROI 502 for all frames 500 within the time interval of interest of the TDI ultrasonic data, as indicated by brackets 564 and 566 on FIG. 11.

In step 456, the signal processor 116 differentiates the extracted velocities to get the corresponding accelerations. In step 458, the signal processor 116 identifies the largest negative acceleration and its associated time within the heart cycle for each cell.

In step 460, the signal processor 116 identifies the cell within the ROI 502 which has the largest negative acceleration. The candidate MVO value 568 is illustrated on TDI velocity curve 556 and corresponds to the timing of the identified cell. Therefore, the candidate MVO value 568 provides a timing value occurring close to the timing of the MVO 166.

Returning to the method of FIG. 4, in step 214 the signal processor 116 searches for the AVC 162 based on the timing of the candidate MVO value 568. By having found the timing of the candidate MVO value 568, a temporal interval for detection of the AVC 162 may be set to avoid acceleration values occurring at or after the MVO 166.

Turning to FIG. 7, in step 600 the signal processor 116 sets the search interval indicated by brackets 572 and 574 on the TDI velocity curve 570 (FIG. 11) for the left AVC. The signal processor 116 also sets the search interval indicated by brackets 578 and 580 on the TDI velocity curve 576. The start of the AVC search interval, indicated by brackets 572 and 578, is set prior to the candidate MVO value 568 based on a first calculated percentage, such as 22%, of the length of the heart cycle. The end of the AVC search interval, indicated by brackets 574 and 580, is set prior to the candidate MVO value 568 based on a second calculated percentage, such as 5%, of the length of the heart cycle. Thus, if the heart rate is 60 beats per minute, the length of the heart cycle would be 1000 milliseconds, and the brackets 572 and 578 would be set at 220 ms prior to the candidate MVO value 568 and the brackets 574 and 580 would be set at 50 ms prior to the candidate MVO value 568. It should be understood that values other than 22% and 5% may be used for the first and second calculated percentages.

Flow passes to step 602 if a spatial search for the AVC 162 is to be accomplished. In step 602, the signal processor 116 defines a region of interest in space for each of the left and right walls of the left ventricle based on the positions of the tracked mitral ring points 516 and 518. Left ROI 508 for the left wall and right ROI 510 for the right wall are illustrated in FIG. 8. The left and right ROIs 508 and 510 are limited to the lower ⅗ part of the frame 500 and are based on the maximum movement or displacement of the mitral ring points 516 and 518.

In step 604, the signal processor 116 extracts the velocities for all cells within the ROIs 508 and 510 for all frames 500 within the time interval of interest of the TDI image, indicated by brackets 572 and 574 on TDI velocity graph 552 and by brackets 578 and 580 on TDI velocity graph 554.

In step 606, the signal processor 116 differentiates the extracted velocities to get the corresponding accelerations. In step 608, the signal processor 116 identifies the time value and the positive acceleration value of the largest positive acceleration for each cell.

In step 610, the signal processor 116 identifies the cell within each of the ROIs 508 and 510 which has the largest positive acceleration. The cells thus identify candidate points 582 and 584 for the left and right walls respectively, indicating both the specific spatial location with the frame 500 and the time within the heart cycle of the AVC 162.

Alternatively, the time estimate for the AVC 162 may be determined using only the velocity/time curves of the mitral ring points 516 and 518. Returning to step 600, flow passes to step 612. In step 612, the signal processor 116 extracts the velocities (not shown) for each of the mitral ring points 516 and 518. In step 614, the signal processor 116 differentiates the extracted velocities of step 612 within the time intervals set in step 600 to get the corresponding accelerations.

In step 616, the signal processor 116 identifies the timing of the largest positive acceleration value for each of the left and right walls. The AVC 162 estimates for each wall are identified, such as candidate points 528 and 584 of step 610.

While the spatial search for the AVC 162 (steps 600-610) and the mitral ring based search for the AVC 162 (steps 600, 612-616) may each be conducted as separate methods, it is also possible to combine the methods. Therefore, after each of the methods is complete, flow passes from the steps 610 and 616 to step 618. In step 618, if the methods are not to be combined, flow returns to step 216 of FIG. 4. In step 618, if the methods are to be combined, flow passes to step 620. It should be understood that a protocol may be established to automatically calculate one or both of the methods. Also, the user may be prompted to input a selection defining which of the methods should be used.

In step 620, the signal processor 116 compares the timing between the two estimates of steps 610 and 616. Lower variability with the mitral ring based method has been found and may be a result that the velocities originating from the positions of the mitral ring points 516 and 518 are robust, as discussed previously. While this ensures that the velocities do originate from the mitral plane, the mitral plane may not be the best location in all cases for detecting AVC effects. In comparison, the spatial search method searches in more locations, which may be advantageous for some anatomies.

In step 622, if the difference between the timing estimates of the two methods exceeds 20 ms, the signal processor 116 chooses the mitral ring based AVC timing of step 616. If the difference between the timing estimates of the two methods is less than or equal to 20 ms, the signal processor 116 chooses the spatial search based AVC timing of step 610. Flow then returns to step 216 of FIG. 4. It should be understood that values other than 20 ms may be used to compare the differences between the timing estimates.

Returning to FIG. 4, in step 216 data is displayed on the display system 118 for review by a user. For example, the frame 500 of FIG. 8 may be displayed. ROIs 502, 508 and 510 are displayed along with the mitral ring points 516 and 518. The spatial locations of detected left AVC 520 and detected right AVC 522 are illustrated along with detected candidate MVO value 524. Lines, boxes, or other markings may used as an overlay to indicate the ROIs 502, 508 and 510, mitral ring points 516 and 518, and the detected left AVC 520, detected right AVC 522, and detected candidate MVO value 524. The overlay may remain displayed on the display system 118 and stationary in contrast to the ultrasonic data which experiences movement while the user cycles through and reviews multiple frames. By way of example only, the frame 500 is the frame in time where the right AVC is detected.

By reviewing the ultrasonic data, overlays, curves, plots, and the like, the user may evaluate the success of the methods previously discussed. For example, failure of the automatic detection of the mitral ring points 516 and 518 may be identified by a user on the display system 118 if the mitral ring points 516 and 518 are more than 1 centimeter from the correct position. The performance of E wave 168 detection can be evaluated by viewing velocity/time curves such as in FIG. 9. The detection of the candidate MVO value 524 may be evaluated by viewing plots such as in FIGS. 8 and 11.

A protocol may be programmed to provide both the left and right AVC estimates to the user. Alternatively, only one estimate may be provided, such as the left AVC. Optionally, the user may select the estimate from the left ventricle wall which is closest to the aortic valve when viewing the data on the display system 118.

Therefore, the aforementioned method and apparatus may be used to automatically or semi-automatically detect cardiac events and the timing of the intervals of the heart within the same heart cycle. When cardiac events and timing intervals are automatically detected, automatic or semi-automated analysis and diagnosis of patient data may be accomplished. Furthermore, once a first cardiac event is found, additional cardiac events can be located based on the first cardiac event. When cardiac events such as AVO 158 and AVC 162 are automatically detected, the search interval for secondary parameters may be set automatically and much more accurately than currently used regression formulas. Examples of such secondary parameters are time-to-peak-velocity as used in tissue synchronicity imaging (TSI), and systolic displacement, which is also referred to as tissue tracking (TT). Other uses of the automatic AVC 162 detection are when calculating end-systolic strain values, post-systolic strain index, and IVR/ES strain index, all of which require an accurate definition of end-systole (AVC 162).

While the invention has been described in terms of various specific embodiments, those skilled in the art will recognize that the invention can be practiced with modification within the spirit and scope of the claims.

What is claimed is:

1. A method for detecting cardiac events, comprising:
   acquiring ultrasonic data comprising a heart cycle;
   detecting tissue velocities associated with said ultrasonic data;
   detecting a value based on said tissue velocities, said value being one of a maximum value and a minimum value;
   identifying a time within said heart cycle associated with said value; and
   detecting a cardiac event with respect to said value and said time, wherein the cardiac event is the opening or closing of a cardiac valve.

2. The method of claim 1, wherein said cardiac event further comprising one of a mitral valve opening, a mitral valve closing, an aortic valve opening, and an aortic valve closing.

3. The method of claim 1, wherein said detecting tissue velocities step is based on one of tissue Doppler information and speckle tracking of ultrasonic B-mode images.

4. The method of claim 1, further comprising:
   defining a region of interest comprising a subset of said ultrasonic data; and
   detecting said value within said region of interest.

5. The method of claim 1, further comprising:
   detecting a cardiac landmark, said cardiac landmark being identified by one of an automatic search detection and a user input; and
   defining a region of interest comprising a subset of said ultrasonic data, said region of interest being located with respect to said cardiac landmark, said value being detected within said region of interest.

6. The method of claim 1, said ultrasonic data further comprising data indicative of a mitral ring, said method further comprising:
   detecting at least one point on said mitral ring; and
   defining a region of interest comprising a subset of said ultrasonic data, said region of interest being located with respect to said mitral ring, said value being detected within said region of interest.

7. The method of claim 1, further comprising:
identifying a temporal search interval based on said value;
identifying a maximum acceleration value based on said tissue velocities of said ultrasonic data within said temporal search interval, said maximum acceleration value being one of a largest positive value and a largest negative value; and
detecting a second cardiac event based on said maximum acceleration value.

8. The method of claim 1, further comprising:
identifying a temporal search interval based on said value, said value being indicative of one of an ECG wave, an E wave interval and an A wave interval;
identifying a maximum acceleration value based on said tissue velocity of said ultrasonic data within said temporal search interval, said maximum acceleration value being one of a largest positive value and a largest negative value; and
detecting a second cardiac event based on said maximum acceleration value.

9. The method of claim 1, wherein detecting a cardiac event comprises automatically detecting the cardiac event.

10. The method of claim 1, further comprising tracking motion of a cardiac landmark to detect tissue velocities.

11. The method of claim 1, further comprising tracking motion of points on a portion of an organ to detect tissue velocities.

12. An apparatus for detecting cardiac events, comprising:
an ultrasonic probe for transmitting and receiving ultrasonic data;
an ECG device for acquiring EGG data associated with said ultrasonic data;
a signal processor configured to process said ultrasonic data, said signal processor detecting one of a maximum and minimum value based on tissue velocities associated with said ultrasonic data, said signal processor identifying a time associated with said one of a maximum and minimum value, said signal processor detecting a cardiac event with respect to said time and said one of a maximum and minimum value, wherein the cardiac event is the opening or closing of a cardiac valve; and
a display for displaying at least one of said ultrasonic data and said EGG data.

13. The apparatus of claim 12, further comprising a user input for defining a point within said ultrasonic data, said one of a maximum and minimum value being detected based on said point.

14. The apparatus of claim 12, further comprising:
said probe further comprising acquiring said ultrasonic data over a heart cycle; and
said signal processor further comprising defining a point of interest within said ultrasonic data and tracking said point of interest over said heart cycle, said signal processor extracting said tissue velocities based on said point of interest.

15. The apparatus of claim 12, further comprising:
said probe further comprising acquiring said ultrasonic data over a heart cycle, said ultrasonic data comprising data indicative of a mitral valve; and
said signal processor further comprising defining a region of interest, said region of interest comprising a subset of ultrasonic data comprising at least a portion of said mitral valve, said one of a maximum and minimum value being based on said subset of ultrasonic data.

16. The apparatus of claim 12, further comprising:
said probe further comprising acquiring said ultrasonic data over a heart cycle, said ultrasonic data comprising data indicative of a mitral valve; and
said signal processor identifying a point in time indicative of an opening of the mitral valve, said signal processor identifying a search interval within said heart cycle being prior to said point in time, said cardiac event being detected within said search interval.

17. The apparatus of claim 12, further comprising:
said probe further comprising acquiring said ultrasonic data over a heart cycle; and
said signal processor identifying one of an E wave and an A wave, said signal processor setting a search interval within said heart cycle prior to one of said B wave and said A wave, said signal processor detecting said one of a maximum and minimum value within said search interval.

18. A method for detecting cardiac events, comprising:
acquiring ultrasonic data comprising a heart cycle;
detecting a first maximum or minimum value based on tissue velocities associated with said ultrasonic data;
locating a search interval based on said first maximum or minimum value, said search interval comprising a portion of said heart cycle;
detecting a second maximum or minimum value based on said tissue velocities within said search interval; and
detecting a cardiac event using said second maximum or minimum value.

19. The method of claim 18, said method further comprising:
identifying a point of interest associated with a cardiac landmark within said ultrasonic data;
extracting tissue velocity data associated with said point of interest within said search interval;
identifying said second maximum or minimum value based on said tissue velocity data; and
identifying a time associated with said cardiac event based on said second maximum or minimum value.

20. The method of claim 18, further comprising:
identifying a point of interest associated with a cardiac landmark within said ultrasonic data;
identifying a region of interest located with respect to said point of interest;
extracting tissue velocity data associated with said region of interest within said search interval; and
detecting said second maximum or minimum value based on said tissue velocity data within said region of interest, said second maximum or minimum value identifying a time and spatial location of said cardiac event.

21. The method of claim 18, further comprising detecting an E wave interval within said heart cycle, said first maximum or minimum value being associated with said B wave interval, said search interval being located prior to said first maximum or minimum value within said heart cycle.

22. The method of claim 18, further comprising:
identifying first and second regions of interest (ROI) located with respect to first and second points of interest;
extracting tissue velocity data associated with said first and second ROIs within said search interval; and
detecting a first ROI maximum or minimum value and a second ROJ maximum or minimum value based on said tissue velocity data within said first and second ROIs.

23. The method of claim 18, further comprising:
  calculating at least one of velocity and acceleration curves based on said tissue velocities; and,
  detecting a value based on said curves, said value being one of a maximum positive and a maximum negative value, said value being used to detect a second cardiac event.

24. The method of claim 18, wherein the detected cardiac event is the opening or closing of a cardiac valve.

* * * * *